United States Patent [19]

Willrett et al.

[11] Patent Number: 4,851,347

[45] Date of Patent: Jul. 25, 1989

[54] BULK STARTER MEDIUM

[75] Inventors: Douglas L. Willrett, Sioux Falls, S. Dak.; Michael Comotto, Green Bay, Wis.

[73] Assignee: Nordica International, Inc., Sioux Falls, S. Dak.

[21] Appl. No.: 52,254

[22] Filed: May 20, 1987

[51] Int. Cl.[4] .......................... C12N 1/20; C12N 1/38; A23C 19/06
[52] U.S. Cl. ................................. 435/252.1; 435/244; 435/252.4; 435/253.6; 426/38; 426/43; 426/61
[58] Field of Search ........... 435/253, 244, 139, 252.1, 435/252.4, 253.6; 426/36, 38, 40, 41, 42, 43, 61

[56] References Cited

U.S. PATENT DOCUMENTS

| | | | |
|---|---|---|---|
| 4,085,228 | 4/1978 | Reinbold et al. | 426/36 |
| 4,372,979 | 2/1983 | Reinbold et al. | 426/36 |
| 4,402,986 | 9/1983 | Sinkoff et al. | 426/41 |
| 4,515,815 | 5/1985 | Kosikowski | 426/40 |

Primary Examiner—Elizabeth C. Weimar
Attorney, Agent, or Firm—Kimmel, Crowell & Weaver

[57] ABSTRACT

The use of a high solids content medium for preparing cheese starter cultures is effective in conditioning the bacteria to enhance their ability to produce cheese from a high solids base. The ingredients of the medium include carbohydrates which are not fermentable by the bacteria, as well as milk protein sources and conventional nutrients. The medium prior to addition of the bacterial starter cultures has a minimum total solids content of about 30%.

7 Claims, No Drawings

BULK STARTER MEDIUM

BACKGROUND OF THE INVENTION

The field of this invention is cheese making and more particularly to a composition and method for propagating a starter culture suitable for use with high solids content milk.

Traditionally, cheese is manufactured from milk consisting of approximately 13% solids and 87% water. Approximately 3.5% of the solids in milk is protein. During cheese manufacture, as a result of the combined action by added enzymes and starter cultures, a large portion of this protein (casein) is precipitated from solution and is mechanically and microbiologically transformed into what we call cheese of many varieties. However, a significant portion of the milk protein (whey proteins) remain in the fluid phase of cheese manufacture (whey) along with other soluble solids such as lactose.

Traditional propagation of bulk starter culture used as one of the principle cheese making ingredients is conducted in a growth medium made up of dairy-derived ingredients such as milk and/or whey solids and various food-grade chemicals. A typical conventional bulk starter medium is described in U.S. Pat. No. 4,402,986 which description is incorporated herein in its entirely by reference.

Culture media generally range from 6–12% total solids. During traditional cheese manufacture the added solids in the form of bulk starter culture are mostly soluble in the whey portion and are not recovered as cheese. Therefore, the use of bulk starter culture is a direct expense in the process of manufacturing cheese.

In more recent times, the technology of membrane separation has been applied to cheese making to radically change this traditional process. The general approach in ultrafiltration cheese making has been to separate whole milk into cream and skim milk and then to subject the skim milk to ultrafiltration concentration and then to recombine the cream with the ultrafiltered concentrate, called retentate. This liquid "precheese" is then inoculated with culture and then set with rennet for conversion to cheese curd. Using the separation techniques of ultrafiltration and reverse osmosis, the solids in milk can be selectively separated and concentrated prior to the fermentation of milk into cheese. As a result of this process all of the protein including casein and whey proteins are recovered as cheese, making this form of manufacture more efficient and profitable. As opposed to traditional cheese making, the added solids in the form of bulk starter culture are generally recovered as cheese solids.

In ultrafiltration processes the concentrated form of milk, herein referred to a retentate, generally consists of up to about 40% total solids. This high concentration of solids introduces new problems to the role of the starter culture in cheese making. The primary role of the cheese starter culture is to produce sufficient lactic acid as a result of the fermentation of milk lactose to reduce the pH of the cheese to approximately 5.0. The high solids of the retentate results in a more inhibitory growth environment for the starter culture that normally is grown in milk at 13% solids; possibly as a result of the higher osmotic pressure provided by the additional solids. In addition, the solids in the retentate produce a greater buffering capacity making it more difficult to effectively reduce the pH to the desired level. These effects require a longer processing time and therefore reduces the economic attractiveness of the ultrafiltration cheese making process. Attempts to shorten the processing time have included increasing the amount of starter inoculum. This, however, dilutes retentate protein thereby lowering the yield gain from the use of ultrafiltration.

Also, salt, which is normally added at the end of traditional cheese making fermentation to arrest the action of the starter culture, is sometimes added to the retentate before the cheese making fermentation, making the retentate even more inhibitory to growth by traditional starter cultures.

An objective of the present invention is the provision of a method of producing a starter culture inoculum suitable for use in cheese making, employing high solids content ultrafiltration retentate.

It is also an objective of the present invention to provide a bulk starter culture which will function in high solids content retentate to produce a cheese product.

It is a further objective of the present invention to provide an improved ultrafiltration method of cheese making wherein a starter culture is utilized which is not inhibited by the high solids content of milk retentate.

It is yet a further objective of the present invention to provide a growth medium which will produce a bulk starter culture that functions in high solids content retentate while retaining high yields.

SUMMARY OF THE INVENTION

The foregoing objects and advantage of the present invention are obtained by using a bulk starter medium having, most preferably, the following composition:

| Ingredient | % By Dry Weight |
| --- | --- |
| Non-fermentable carbohydrates | 45–50 |
| Milk protein sources | 20–35 |
| Growth stimulant | 2–10 |
| Phosphate and/or citrate salts | up to 5 |
| Sodium chloride | up to 2 |
| Stabilizer | up to 1 |

Preferably the composition and method of the present invention utilizes non-fermentable carbohydrates such as sucrose, dextrins, and maltodextrins. The preferred milk protein sources are casein, caseinates, and whey protein concentrates. The fermentable carbohydrate sources can be selected from glucose, lactose, permeate solids, whey solids and milk solids. The growth stimulants can be selected from various yeasts, yeast extracts, hydrolyzed casein, and other hydrolyzed proteins and the stabilizer can be starch.

The more preferred composition for the practice of the present invention is as follows.

| Ingredient | % By Dry Weight |
| --- | --- |
| Maltodextrin | 45–50 |
| Sodium caseinate | 20–25 |
| Sweet whey powder | 5–10 |
| Whey protein concentrate | 5–10 |
| Nonfat dry milk | 3–5 |
| Dried yeast solids | 2–4 |
| Sucrose | 2–3 |
| Diammonium phosphate | 1–2 |
| Sodium citrate | 1–2 |
| Sodium chloride | up to 2 |
| Monoammonium phosphate | up to 1 |

-continued

| Ingredient | % By Dry Weight |
| --- | --- |
| Starch | up to 1 |

It has been discovered that by propagating starter cultures in the described growth medium which contains a high solids content, typically greater than or equal to 17% solids. Where the culture is grown under condition of pH control, it is possible to produce a bulk starter culture that was better suited for efficiently ferment high solids content retentate to the desired pH as compared to starter culture traditionally grown in bulk starter media containing lower total solids content.

In addition, the growth of multiple strain cultures in the described high solids medium is more evenly balanced, i.e., relatively more equal portions of the strains produced, than occurs with multiple strain cultures grown in traditional lower solids content media.

Finally, the use of ultra high solids bulk culture turns the use of bulk culture from a direct expense to a form of increased profit in the form of added cheese solids.

It is well documented in the scientific literature that large physiological changes such as pH shifts, temperature shifts and the like often result in an adjustment period for a culture to regain its normal fermentation capabilities. It is felt that this same adjustment time is required when starter is propagated in a low solids medium and then added to a 40% solids fermentation medium such as ultrafiltration retentate. However, surprisingly, when these same cultures are grown in an ultra high solids medium, preferably at least 17% solids and as high as approximately 40% total solids, the cells are pre-conditioned to this high solids environment and when subsequently added to the retentate, their adjustment period is shorter than normally expected.

The following examples illustrate the efficacy of the bulk starter medium of the present invention.

EXAMPLE I

Commercial culture strains 804, 805 and 106B (NORDICA International, Inc.) were propagated in the commercial bulk starter medium White Cold (NORDICA International, Inc.) which had been reconstituted to 8.7% total solids. Bulk culturing was done at 27° C. under conditions of external pH control (controlling pH 6.0 using ammonium hydroxide). Activity (measure of ability to reduce pH) was measured after 4 hour incubation at 32° C. in both traditional solid milk (RSM; 11%ts) and retentate (produced by ultrafiltration to approximately 40%ts) with added salt. The total activity measured in the salted retentate was divided by the total activity in traditional solids milk to give a percentage of the total activity achieved when grown in retentate. The percentage of total activity for White Gold bulk culture was 44.66%.

When the same culture combination was grown in the culture media described in TABLE I (30%ts) using the same conditions as with White Gold, the resulting percentage of total activity was 52.59%; a substantial improvement over White Gold.

Again, using the same culture conditions, but bulk culturing in unsalted retentate (30%ts), the resulting percentage of total activity was only 38.86%; suggesting it is not merely bulk culturing in a medium containing 30% total solids, but the particular composition of solids that is important to achieve higher activity.

To further substantiate the importance of the composition of the medium, when unsalted retentate was supplemented with several of the solids used in the media of TABLE I, the resulting percentage of total activity improved to 50.94%.

Finally, when a low solids version (7.3%ts) of the media of TABLE I which did contain added sodium chloride was used, the percentage of total activity was 50.70%. This result strongly suggests that pre-conditioned growth in the presence of sodium chloride is also responsible for the improved activity in the salted retentate

TABLE I

| Ingredient | Grams/Liter | % of Dry Weight |
| --- | --- | --- |
| Maltodextrin | 205 | 47.68 |
| Sodium caseinate | 100 | 23.26 |
| Sweet whey powder | 35 | 8.15 |
| Whey protein concentrate | 29 | 6.74 |
| Nonfat dry milk | 17 | 3.95 |
| Dried yeast solids | 13 | 3.02 |
| Sucrose | 10 | 2.33 |
| Diammonium phosphate | 7.5 | 1.74 |
| Sodium citrate | 5 | 1.16 |
| Sodium chloride | 5 | 1.16 |
| Monoammonium phosphate | 2.5 | 0.58 |
| Starch | 1 | 0.23 |
|  | 430.00 | 100.00 |

EXAMPLE II

Using the same conditions as in Example I, but growing only the single strain 706 (NORDICA International, Inc.) the measured activity in traditional solids milk of the culture grown in a low solids medium was nearly the same as the activity of the same strain grown ion the media of TABLE I (30%ts); 1.45 as opposed to 1.41, respectively. However, comparison of activities in salted retentate clearly shows the poised condition of the high solids grown culture (0.45) as opposed to the low solids culture (0.3).

EXAMPLE III

Population analysis of each of the cultures described in Example I further demonstrated the superior performance of the ultra high solids media. The White Gold culture consisted of 60%–805, 40%–106B, and 0%–804. The unsalted retentate was totally unbalanced consisting of 100%–106B. The low solids version with sodium chloride was also unbalanced made up of 95%–106B and only 5%–804. However, both the ultra high solids media, and the supplemented unsalted retentate had nearly the same strain balances, 55%–106B, 34%–805, 11%–804 and 58%–106BB, 29%–805, 13%–804, respectively.

It is advantageous in cheese making to use a balanced bulk culture as opposed to an unbalanced culture in the event of bacteriophage infection of the stater culture.

The greater culture balance achieved by the two formulated ultra high solids media was clearly illustrated by these data.

The products and method described specifically herein are illustrative only and the scope of the present invention is only intended to be limited to the appended claims in view of the applicable prior art.

We claim:

1. A precondition inoculum suitable for use in cheese making using high solids content retentate comprising a preselected cheese making culture grown in a medium consisting essentially of between about 30% and about 40% by weight of the following composition:
about 45% to about 50% carbohydrates not fermentable by the culture used;
about 20% to about 40% milk protein sources;
about 2% to about 10% growth stimulant;
up to about 5% phosphate and/or citrate salts;
up to about 2% sodium chloride; and
up to about 1% stabilizer, wherein said medium is made up in solution to a solids concentration of from about 30% total solids to about 40% total solids, whereby said preconditioned inoculum exhibits similar growth rates in high solids content ultrafiltration retentate to growth rates of inoculum used in low solids content cheese making materials.

2. A preconditioned inoculum suitable for use in cheese making from high solids content retentate comprising a preselected cheese making culture grown in a medium consisting essentially of between about 30% and about 40% by weight of the following composition:
about 45% to about 50% maltodextrin;
about 20% to about 25% sodium caseinate;
about 5% to about 10% sweet whey powder;
about 5% to about 10% whey protein concentrate;
about 3% to about 5% nonfat dry milk;
about 2% to about 4% dried yeast solids;
about 2% to about 3% sucrose;
about 1% to about 2% diammonium phosphate;
about 1% to about 2% sodium citrate;
up to about 2% sodium chloride;
about 1% monoammonium phosphate; and up to about 1% starch, wherein said medium is made up in solution to a solids concentration of from about 30% total solids to about 40% solids, whereby said preconditioned inoculum exhibits similar growth rates in high solids content ultrafiltration retentate to growth rates of inoculum used in low solids content cheese making materials.

3. A method of producing a preconditioned inoculum for use in cheese making using high solids content ultrafiltration retentate comprising the steps of:
selecting a bacterial culture suitable for use in cheese making; and
growing said culture in a growth medium comprising between about 30% and about 40% by weight of the following composition:
about 45% to about 50% carbohydrates which are not fermentable by the bacterial culture selected;
about 20% to about 40% milk protein sources;
about 2% to about 10% growth stimulant;
up to about 5% phosphate and/or citrate salts;
up to about 2% sodium chloride; and
up to about 1% stabilizer, wherein said growth medium is made up in solution to a solids concentration of from about 30% total solids to about 40% total solids and said inoculum demonstrates similar growth rates with high solids content retentate as inoculum that is suitable for with low solids content cheese making materials.

4. A method of producing a preconditioned inculum for use in cheese making using high solids content ultrafiltration retentate comprising the steps of:
selecting a bacterial culture suitable for use in cheese making; and
growing said culture in a growth medium comprising between about 30% and about 40% by weight of the following composition:
about 45% to about 50% maltodextrin;
about 20% to about 25% sodium caseinate;
about 5% to about 10% sweet whey powder;
about 5% to about 10% whey protein concentrate;
about 3% to about 5% nonfat dry milk;
about 2% to about 4% dried yeast solids;
about 2% to about 3% sucrose;
about 1% to about 2% diammonium citrate;
about 1% to about 2% sodium citrate;
up to about 2% sodium chloride,
about 1% monoammonium phosphate; and up to about 1% starch, wherein said growth medium is made up in solution to a solids concentration of from about 30% total solids to about 40% total solids and said inoculum demonstrates similar growth rates with high solids content retentate as inoculum that is suitable for use with low solids content cheese making materials.

5. The method of claim 3 or 4 wherein said growth is conducted at a preselected pH range.

6. A culture media for producing bacterial starters suitable for use in cheese making from high solids ultrafiltration retentate comprising on a dry weight basis from:
about 45% to about 50% carbohydrates which are not fermentable by the bacteria to be started;
about 20% to about 40% milk protein sources;
about 2% to about 10% growth stimulant;
up to about 5% phosphate and/or citrate salts
up to about 2% sodium chloride; and
up to about 1% stabilizer, wherein said media is made up in solution to a solids concentration of from about 30% total solids to about 40% total solids before use in a high solids ultrafiltration retentate in making cheese.

7. A culture media for producing bacterial starters comprising on a dry weight basis from:
about 45% to about 50% maltodextrin;
about 20% to about 25% sodium caseinate;
about 5% to about 10% sweet whey powder;
about 5% to about 10% whey protein concentrate;
about 3% to about 5% nonfat dry milk;
about 2% to about 4% dried yeast solids
about 2% to about 3% sucrose
about 1% to about 2% diammonium phosphate;
about 1% to about 2% sodium citrate;
up to about 2% sodium chloride;
about 1% monoammonium phosphate; and
up to about 1% starch wherein said media is made up in solution to a solids concentration of from about 30% total solids to about 40% total solids.

* * * * *